(12) United States Patent
Colgan

(10) Patent No.: US 11,491,083 B2
(45) Date of Patent: Nov. 8, 2022

(54) INSULIN STORAGE AND DISPENSING SYSTEM

(71) Applicant: Jack Wayne Colgan, Safety Harbor, FL (US)

(72) Inventor: Jack Wayne Colgan, Safety Harbor, FL (US)

(*) Notice: Subject to any disclaimer, the term of this patent is extended or adjusted under 35 U.S.C. 154(b) by 0 days.

(21) Appl. No.: 17/588,157

(22) Filed: Jan. 28, 2022

(65) Prior Publication Data

US 2022/0241150 A1   Aug. 4, 2022

Related U.S. Application Data

(60) Provisional application No. 63/143,480, filed on Jan. 29, 2021.

(51) Int. Cl.
| | | |
|---|---|---|
| *A61M 5/178* | (2006.01) | |
| *A61M 5/315* | (2006.01) | |
| *A61J 1/00* | (2006.01) | |
| *A61J 1/16* | (2006.01) | |
| *A61J 1/20* | (2006.01) | |
| *B65D 85/42* | (2006.01) | |
| *A61M 5/00* | (2006.01) | |
| *A61B 50/20* | (2016.01) | |

(52) U.S. Cl.
CPC .............. *A61J 1/165* (2013.01); *A61M 5/003* (2013.01); *A61B 50/20* (2016.02); *A61J 1/2065* (2015.05); *A61J 1/2096* (2013.01); *A61M 5/002* (2013.01); *A61M 5/008* (2013.01); *A61M 5/1782* (2013.01); *A61M 2205/58* (2013.01); *B65D 85/42* (2013.01)

(58) Field of Classification Search
CPC ..... A61B 50/20; A61B 50/33; A61B 2050/21; A61M 2205/58; A61M 5/003; A61M 5/008; A61M 5/14; A61M 5/1782; A61J 1/165; A61J 1/16; A61J 1/20; A61J 1/2065; B65D 1/36; B65D 81/133; B65D 85/42
USPC ..... 62/132; 141/27, 233, 375, 330; 206/364, 206/365, 565, 571; 211/71.01, 85.13, 74; 222/181.2; 248/311.2, 311.3, 176.1; 604/414, 181, 407
See application file for complete search history.

(56) References Cited

U.S. PATENT DOCUMENTS

| | | | | |
|---|---|---|---|---|
| 2,659,485 | A * | 11/1953 | Duley .................. | A61M 5/008 206/564 |
| 2,677,372 | A * | 5/1954 | Barnish, Jr. ........... | A61J 1/2096 D24/128 |
| 2,887,215 | A * | 5/1959 | Hutchison ............. | B65D 81/133 206/586 |
| 3,606,006 | A * | 9/1971 | Raybois ................. | B65D 85/42 206/561 |
| 3,610,241 | A * | 10/1971 | LeMarie ............. | A61M 5/1782 604/407 |
| 3,833,030 | A * | 9/1974 | Waldbauer, Jr. ..... | A61M 5/1782 141/26 |
| 3,844,318 | A * | 10/1974 | Raia ..................... | A61M 5/1782 604/116 |

(Continued)

*Primary Examiner* — Gideon R Weinerth
(74) *Attorney, Agent, or Firm* — Sandra L. Layer

(57) ABSTRACT

An insulin storage and dispensing system for housing a standard insulin bottle and securely keeping the bottle in place when using a syringe to access the port on the top of the bottle to fill the syringe while providing accessibility in the form of a convenient mounting assembly for mounting on a refrigerator, an interior cabinet door or wall.

6 Claims, 3 Drawing Sheets

(56) References Cited

U.S. PATENT DOCUMENTS

| | | | | |
|---|---|---|---|---|
| 3,853,158 A * | 12/1974 | Whitty | A61M 5/1782 | 141/330 |
| 3,982,716 A * | 9/1976 | Trees | A61M 5/1417 | 248/309.4 |
| 3,993,063 A * | 11/1976 | Larrabee | A61J 1/2096 | 604/197 |
| 4,252,159 A * | 2/1981 | Maki | A61J 1/2096 | 141/95 |
| 4,278,225 A * | 7/1981 | Phelps | A61M 5/008 | D8/371 |
| 4,439,193 A * | 3/1984 | Larkin | A61M 39/14 | 604/407 |
| 4,475,915 A * | 10/1984 | Sloane | A61M 5/1782 | 141/27 |
| 4,489,766 A * | 12/1984 | Montada | A61M 5/31525 | 604/407 |
| 4,778,454 A * | 10/1988 | LaDow | A61J 1/2096 | 604/407 |
| 5,402,889 A * | 4/1995 | Hermann | B65D 5/4233 | 206/443 |
| 5,468,233 A * | 11/1995 | Schraga | A61M 5/1782 | 604/407 |
| 5,474,178 A * | 12/1995 | DiViesti | H01R 43/00 | 206/723 |
| 5,487,738 A * | 1/1996 | Sciulli | A61M 5/1782 | 141/27 |
| 5,531,702 A * | 7/1996 | Baker | A61M 5/008 | 211/85.13 |
| 5,542,760 A * | 8/1996 | Chanoch | A61M 5/1782 | 604/82 |
| 5,873,859 A * | 2/1999 | Muntz | A61J 1/2096 | 604/407 |
| 6,006,798 A * | 12/1999 | Lindquist | A61M 5/1782 | 141/369 |
| 6,162,199 A * | 12/2000 | Geringer | A61M 5/1782 | 604/407 |
| 6,364,866 B1 * | 4/2002 | Furr | A61M 5/1782 | 141/330 |
| 6,439,276 B1 * | 8/2002 | Wood | A61M 5/3205 | 141/97 |
| 6,497,697 B1 * | 12/2002 | Cohn | A61M 5/1782 | 141/330 |
| 6,808,149 B1 * | 10/2004 | Sendowski | A61J 1/16 | 248/312 |
| 7,677,275 B2 * | 3/2010 | Witte | A61M 5/1782 | 141/330 |
| 8,360,114 B2 * | 1/2013 | Clark | A61J 1/2096 | 141/330 |
| D695,546 S * | 12/2013 | Kruger | A61M 5/008 | D6/534 |
| 9,132,927 B1 * | 9/2015 | Larson | A61J 1/2096 | |
| 9,144,465 B2 * | 9/2015 | Hunkeler | A61B 50/30 | |
| 9,878,098 B1 * | 1/2018 | Opland | A61M 5/1782 | |
| 10,342,736 B2 * | 7/2019 | Sharpe | A61J 1/16 | |
| D945,277 S * | 3/2022 | Hu | A61J 1/2096 | D9/750 |
| 11,284,961 B2 * | 3/2022 | Whelan | A61B 50/20 | |
| 2002/0124905 A1 * | 9/2002 | Draughn | A61J 1/16 | 141/25 |
| 2004/0004171 A1 * | 1/2004 | Beal | A61J 1/16 | 248/311.2 |
| 2004/0144903 A1 * | 7/2004 | Cherubini | A61J 1/2096 | 248/176.1 |
| 2005/0087256 A1 * | 4/2005 | Clark | A61J 1/2096 | 141/97 |
| 2010/0160890 A1 * | 6/2010 | McOwen | A61J 1/2096 | 604/415 |
| 2013/0092585 A1 * | 4/2013 | Ramirez | B65D 85/42 | 206/419 |
| 2019/0117516 A1 * | 4/2019 | Metz | A61J 1/2096 | |
| 2019/0135509 A1 * | 5/2019 | Biskupski | A61J 1/16 | |
| 2020/0108188 A1 * | 4/2020 | Bell | A61M 5/008 | |
| 2021/0228302 A1 * | 7/2021 | Angot | A61B 50/33 | |
| 2022/0241150 A1 * | 8/2022 | Colgan | A61J 1/165 | |

* cited by examiner

INSULIN STORAGE AND DISPENSING SYSTEM

RELATED APPLICATION

The present patent application claims priority to the corresponding provisional patent application Ser. No. 63/143,480 entitled "INSULIN STORAGE AND DISPENSING SYSTEM" filed on Jan. 29, 2021.

BACKGROUND OF THE INVENTION

Field of the Invention

The present invention relates to an insulin bottle storage and dispensing system and more particularly pertains to a system to assist in the storage and dispensing of insulin. The storage and dispensing being done in a safe, convenient and economical manner.

DESCRIPTION OF THE PRIOR ART

The use of other insulin storage and dispensing systems is known in the prior art. More specifically, other insulin storage and dispensing systems previously devised and utilized for the purpose of storing and dispensing insulin are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe an insulin bottle storage and dispensing system that allows for convenient, safe and economic assistance storing and dispensing insulin.

In this respect, the insulin bottle storage and dispensing system according to the present invention substantially departs from the conventional concepts and designs of the prior art, and in doing so provides an apparatus primarily developed for the purpose of the storage and dispensing of insulin. The storage and dispensing being done in a safe, convenient and economical manner.

Therefore, it can be appreciated that there exists a continuing need for a new and improved insulin bottle storage and dispensing system which can be used for the storage and dispensing of insulin. In this regard, the present invention substantially fulfills this need.

SUMMARY OF THE INVENTION

In view of the foregoing disadvantages inherent in the known types of insulin storage and dispensing systems now present in the prior art, the present invention provides an improved insulin bottle storage and dispensing systems. As such, the general purpose of the present invention, which will be described subsequently in greater detail, is to provide a new and improved insulin storage and dispensing system and method which has all the advantages of the prior art and none of the disadvantages.

To attain this, for a broad perspective, the present invention essentially comprises a rectangular housing with an open front. The housing separated into an upper and lower compartment. The upper compartment configure to receive and retain a standard insulin bottle. The sides of the upper compartment are cutout to allow grasping the insulin bottle for installation and removal. The lower compartment configured to receive the upper portion of a syringe, aligning the needle with the port of the insulin bottle for dispensing.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved insulin storage and dispensing system which has all of the advantages of the prior art insulin storage and dispensing systems and none of the disadvantages.

It is another object of the present invention to provide a new and improved insulin storage and dispensing system which may be easily and efficiently manufactured and marketed.

It is a further object of the present invention to provide a new and improved insulin storage and dispensing system which is of durable and reliable constructions.

It is another object of the present invention to provide a new and improved insulin storage and dispensing system that is convenient for the user and includes multiple mounting choices.

It is still another object of the present invention to be allow for use with various size syringes and bottles.

An even further object of the present invention is to provide a new and improved insulin storage and dispensing system which is susceptible of a low cost of manufacture with regard to both materials and labor, and which accordingly is then susceptible of low prices of sale to the consuming public, thereby making such insulin storage and dispensing system economically available to the buying public.

Lastly, it is an object of the present invention to provide an insulin bottle storage and dispensing system that allows for the convenient, safe and economic storing and dispensing of insulin.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
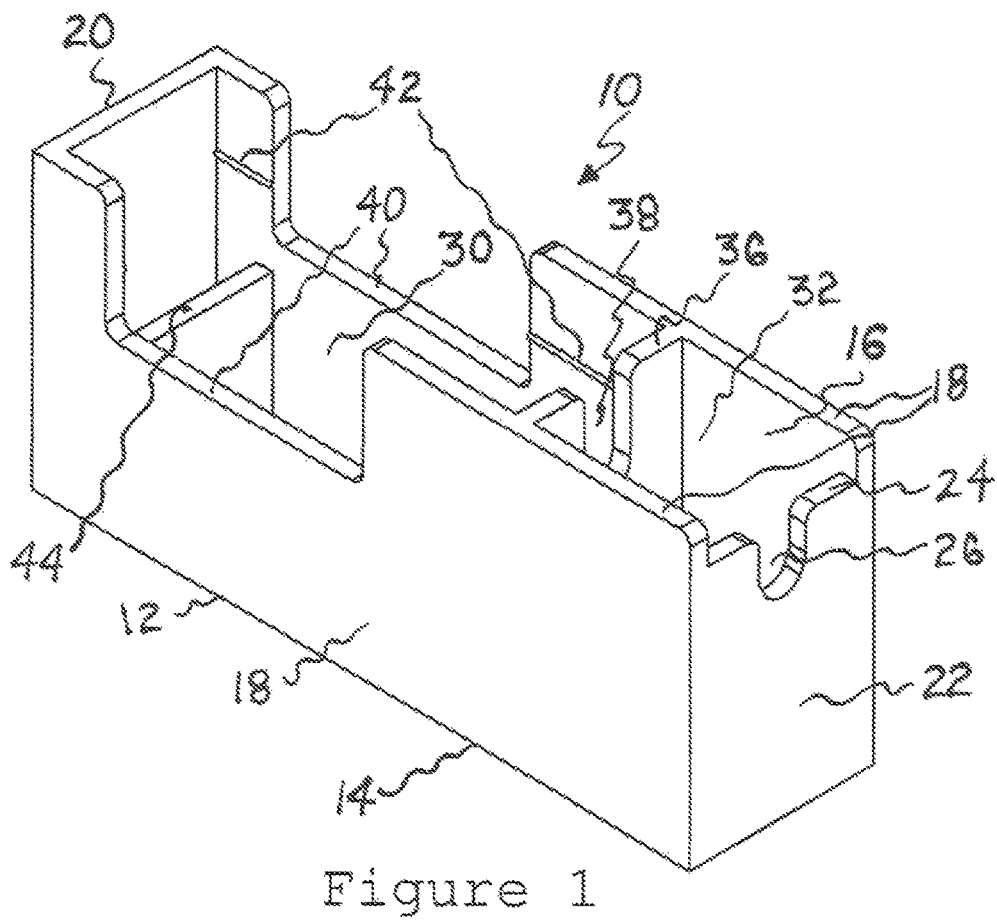
FIG. 1 is a plan view of an Insulin Bottle Storage and Dispensing system constructed in accordance with the principles of the present invention.
Figure 2:
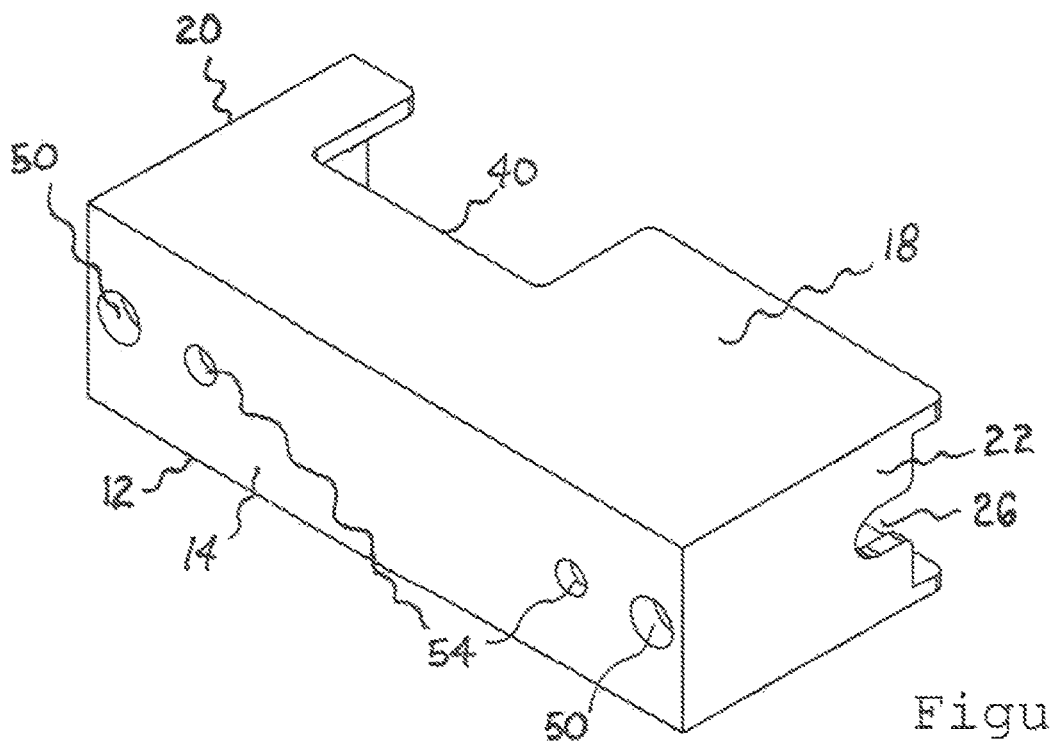
FIG. 2 is a plan view of the back of an Insulin Bottle Storage and Dispensing System.
Figure 3:
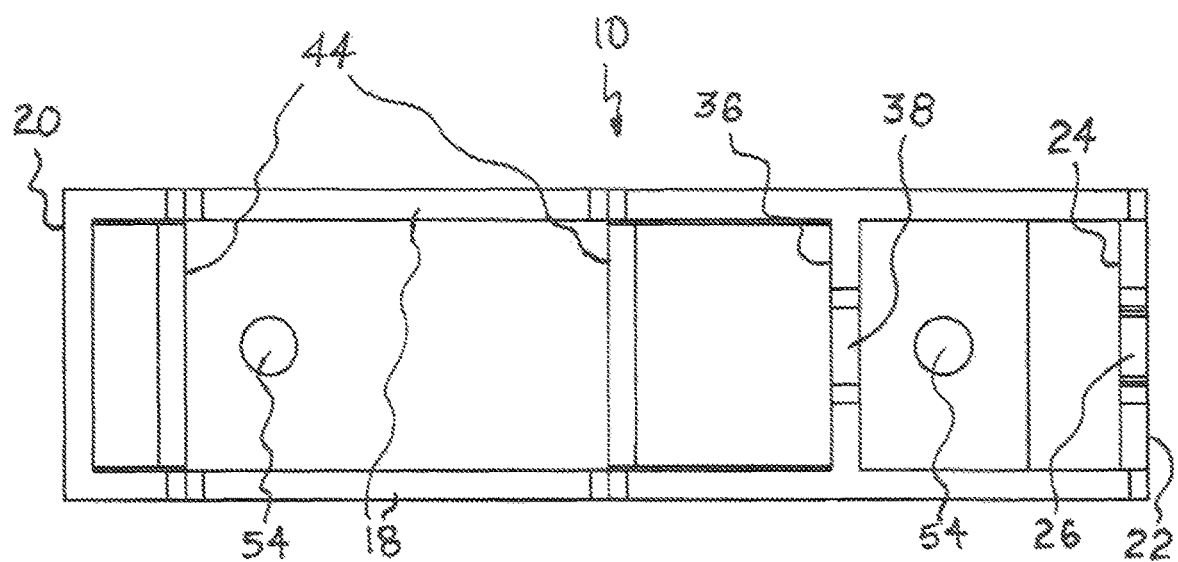
FIG. 3 is a front view of an Insulin Bottle Storage and Dispensing System.
Figure 4:
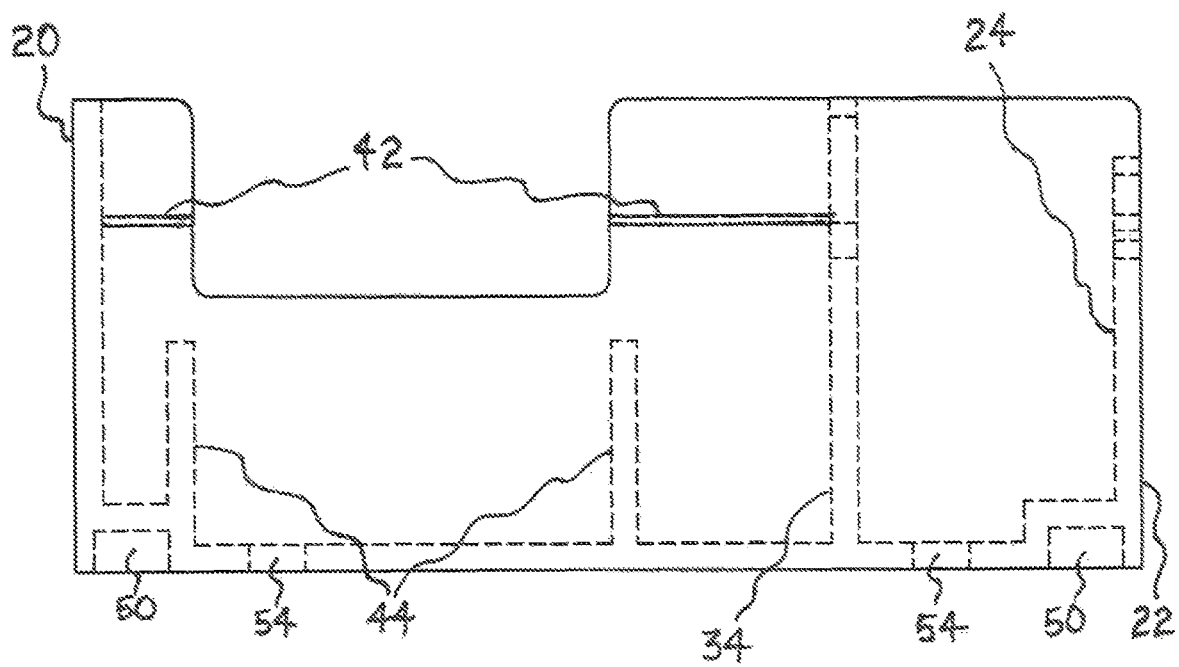
FIG. 4 is a cross-sectional side view of an Insulin Bottle Storage and Dispensing System.
Figure 5:
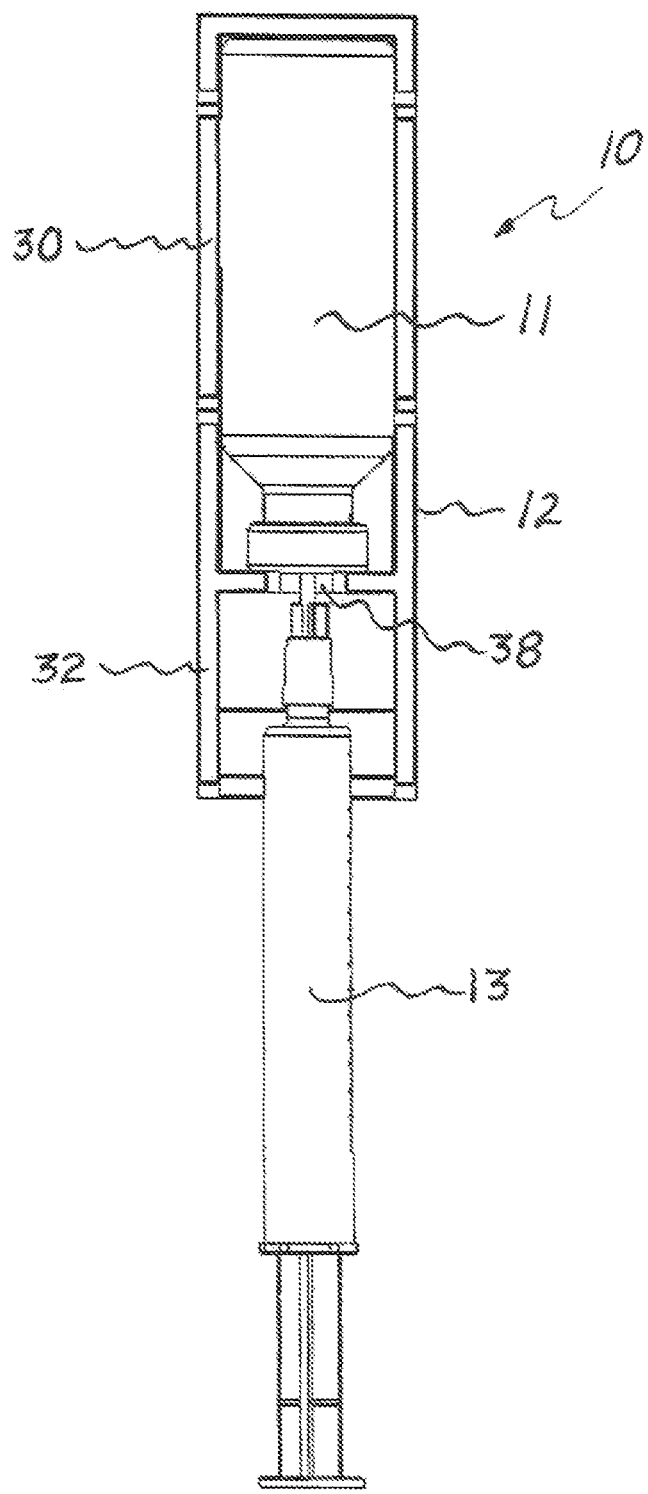
FIG. 5 is a front view of an Insulin Bottle Storage and Dispensing system in use.

With reference now to the drawings, and in particular to FIGS. 1-5 thereof, the preferred embodiment of the new and improved insulin storage and dispensing system embodying the principles and concepts of the present invention and generally designated by the reference numeral 10 will be described.

The present invention, the Insulin Bottle Storage and Dispensing system 10 is comprised of a plurality of components. Such components are individually configured and correlated with respect to each other so as to attain the desired objective. In their broadest context such include an insulin bottle, a syringe and a housing formed to hold the insulin bottle in an inverted position, the top of the insulin bottle resting on a lower shelf, the bottom the housing and the shelf formed with slots to allow access to the top of the bottle and aligning the syringe for dispensing and a means for mounting. In this broad context, first provided is a rectangular housing 12 having a closed back 14, an open front 16, two parallel sides 18 and a parallel top 20 and bottom 22. The housing is formed with an upper compartment 30 for holding an inverted insulin bottle and a lower compartment 32 for aligning the syringe when accessing the top of the insulin bottle. Cutouts are formed in the bottom of the upper compartment and the bottom of the lower compartment to provide access to the port on the top of the insulin bottle and to align the syringe. Rectangular side cutouts 40 are formed in the top half of each of the two sides adjacent to the front side edges allow access to the insulin bottle for placement and removal. A retaining ridge is formed on the interior of each of the sides of the housing for frictionally keeping the bottle in place. Central and upper interior shelves, each having a front edge midway between the closed back and the open front, act a bottle stop to keep the bottle positioned forward in the housing. The bottle stop allows for the two sides to be wide enough to allow sufficient gripping space when hand held. Mounting support is included in the form of two recessed magnets in the closed back adjacent to the top and bottom edges for removably attaching to a metal vertical surface such as the exterior of a refrigerator.

An alternative mounting system is provided in the form of two apertures located in the closed back below the top recess and above the bottom recess for mounting using two screws to attach to a solid vertical surface such as a wooden cabinet door.

Such components are individually configured and correlated with respect to each other so as to attain the desired objective.

From a specific perspective, the invention of the present application the insulin bottle storage and dispensing system shown in FIGS. 1 through 5 is comprised of a housing 12 for use with an insulin bottle 11 having a top port for access and a syringe 13. The housing 12 is adapted to hold the insulin bottle 11 for storage and align the syringe 13 when filling the syringe for use. The housing is rectangular with a closed back 14, an open front 16, two parallel sides 18 and a parallel top 20 and bottom 22. The housing is formed with an upper compartment 30 for holding an inverted insulin bottle and a lower compartment 32 for aligning the syringe when accessing the top of the insulin bottle. The closed back and open front are separated by a first distance. The top and the two parallel sides have front edges parallel with the open front. The bottom of the upper compartment is formed with a lower interior shelf 36. The lower interior shelf 36 has a front edge parallel with the open front. A semi-rectangular cutout 38 with a semi-circular interior edge extends inward from the front edge of the lower interior shelf.

Rectangular cutouts 40 are formed in each of the sides of the upper compartment adjacent to the front side edges. Each of the cutouts has an upper edge and a lower edge. The cutouts providing access to insert and remove the insulin bottle.

Retaining ridges 42 are formed on the interior of each of the sides in the upper compartment between the top and the lower edge of the top of the cutouts and between the upper edge of the bottom of the cutouts and the lower interior shelf for frictionally keeping the bottle in place. Central and upper interior shelves 44 each having a front edge midway between the closed back and the open front act as a bottle stop to keep the bottle stable between the retaining ridges 42 and the front edge of the upper and central shelves while providing adequate distance between the closed back and open front for the two sides to be wide enough to allow sufficient gripping space when hand held.

The bottom is formed with a front edge 24, a second distance separating the closed back and the bottom front edge, the second distance being shorter than the first distance. The bottom front edge 24 is recessed from the open front to allow visibility when accessing the top of the insulin bottle. A semi-rectangular cutout 26 with a semi-circular interior edge extending inward from the bottom front edge 24 parallel to and in line with the semi-rectangular cutout of the lower interior shelf 36 for aligning the syringe for dispensing with the top port of the bottle. In the preferred embodiment, the semi-rectangular cutout 26 of the bottom is formed with a diameter that decreases from the front edge to the back of the semi-circular interior edge to accommodate and restrict movement of syringes of varying diameters while still aligning the needle with the semi rectangular cutout of the lower interior shelf and the port on the top of the insulin bottle. The decreasing diameter acts as guide causing smaller diameter syringes to be held at the rear of the cutout and larger diameter syringes held closer to the front edge.

The closed back is formed with two recesses adjacent to the top and bottom. In the preferred embodiment the recesses are circular. Magnets 50 are housed in the recesses for the purpose of removably attaching to a metal surface such as the exterior of a refrigerator. Two apertures (54) are formed in the closed back interior and adjacent to the two recesses to allow attachment to a vertical surface such as a cabinet door using screws. Alternately the housing could be mounted using an adhesive or adhesive system such as glue, Velcro™ or mounting tape.

A standard insulin bottle having a top port for access and a syringe are provided for use with the housing. The insulin bottle fitting inside the housing in the upper compartment. The bottle is retained by the upper and lower ridges. The syringe having a diameter less than the diameter of the semi-rectangular cutout of the bottom, the lower cutout acting as a guide for the syringe, aligning the needle with the top of the insulin bottle for filling.

The Insulin Storage and Dispensing system is meant to assist an insulin user in the storage and dispensing of insulin by housing a standard insulin bottle and securely keeping the bottle in place when using a syringe to access the port on the top of the bottle to fill the syringe while providing accessibility in the form of a convenient mounting assembly for mounting on a refrigerator, an interior cabinet door or wall. The Insulin Assist assembly provides proper positioning of the bottle to align the needle with the center of the sealed port without interference from the housing. The cutouts in the lower shelf and bottom are of such a size to allow all standard syringes to be used while properly positioning the syringe. The recessed bottom of the housing provides additional visibility when positioning the syringe for filling. The side cutouts allow access for installation and removal of the insulin bottles. The 'stand-off' dimension allow for a safe and adequate distance from the mounting surface to allow a person's hands to have sufficient space for gripping the housing and/or syringe without interfering with the syringe when aligning and filling. Wall thickness of the housing is consistent throughout providing a solid structure and adequate support to keep the bottle and syringe steady. The mounting magnets are of sufficient strength to bond to a metal surface preventing movement and are recessed in order to retain the flat surface of the back of the housing for additional stability and to allow adhesive mounting. The screw holes allow for permanent mounting on a solid surface such as the back of a cabinet door. The housing can be formed of ABS plastic to allow recycling to reduce scrap.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An Insulin Bottle Storage and Dispensing system to assist in the storage and dispensing of insulin, the system comprising in combination:
   a rectangular housing having a closed back, an open front, two parallel sides, a top and a bottom, the top and the bottom being parallel, a first distance between the closed back and the open front, the two parallel sides having front side edges parallel with the open front, a cutout formed in the top half of each of the two parallel sides extending inward from the front side edges, each of the cutouts having an upper edge and a lower edge;
   a lower interior shelf having a front edge parallel with the open front, a semi-rectangular cutout with a semi-circular interior edge extending inward from the front edge of the lower interior shelf;
   an upper retaining ridge formed on the interior of each of the two parallel sides between the top and the upper edge of each of the cutouts parallel to the front side edges, an interior lower retaining ridge formed on the interior of each of the two parallel sides between the lower edge of each of the cutouts and the lower interior shelf parallel to the front side edges and in line with the upper retaining ridge;
   an upper interior shelf and a central interior shelf each having a front edge midway between the closed back and the open front;
   the bottom having a front edge, a second distance between the closed back and the bottom front edge, the second distance being shorter than the first distance, a semi-rectangular cutout with a semi-circular interior edge extending inward from the front edge of the bottom, parallel to and in line with the semi-rectangular cutout of the lower interior shelf.

2. The Insulin Bottle Storage and Dispensing system of claim 1 wherein the closed back is formed with two recesses adjacent to the top and bottom, with magnets housed in the recesses.

3. The Insulin Bottle Storage and Dispensing system of claim 1 further including two apertures formed in the closed back adjacent to the top and bottom.

4. The Insulin Bottle Storage and Dispensing system of claim 1 including a means for mounting the rectangular housing to a vertical surface including a wall, a cabinet, or a refrigerator.

5. The Insulin Bottle Storage and Dispensing system of claim 1 wherein the semi-rectangular cutout with the semi-circular interior edge extending inward from the front edge of the bottom is formed with a diameter that decreases from the front edge to the back of the semi-circular interior edge to accommodate syringes of varying diameters.

6. An Insulin Bottle Storage and Dispensing system to assist in the storage and dispensing of insulin, the system comprising in combination:
   a rectangular housing having a closed back, an open front, two parallel sides, a top and a bottom, the top and the bottom being parallel, a first distance between the closed back and the open front, the two parallel sides having front side edges parallel with the open front, a cutout formed in the top half of each of the two parallel sides extending inward from the front side edges, each of the cutouts having an upper edge and a lower edge;
   a lower interior shelf having a front edge parallel with the open front, a semi-rectangular cutout with a semi-circular interior edge extending inward from the front edge;
   an upper retaining ridge formed on the interior of each of the two parallel sides between the top and the upper edge of each of the cutouts parallel to the front side edges, an interior lower retaining ridge formed on the interior of each of the two parallel sides between the lower edge of each of the cutouts and the lower interior shelf parallel to the front side edges and in line with the upper retaining ridge;

an upper interior shelf and a central interior shelf each having a front edge midway between the closed back and the open front;

the bottom having a front edge, a second distance between the closed back and the bottom front edge, the second distance being shorter than the first distance, a semi-rectangular cutout with a semi-circular interior edge extending inward from the front edge of the bottom, parallel to and in line with the semi-rectangular cutout of the lower interior shelf;

the closed back formed with two recesses adjacent to the top and the bottom, magnets housed in the two recesses, two apertures formed in the closed back interior to the two recesses; and a standard insulin bottle having a top port for access and a syringe.

\* \* \* \* \*